United States Patent [19]

Pagano et al.

[11] Patent Number: 5,242,906
[45] Date of Patent: Sep. 7, 1993

[54] ANTISENSE OLIGONUCLEOTIDES AGAINST EPSTEIN-BARR VIRUS

[75] Inventors: Joseph S. Pagano, Chapel Hill; Nancy R. Traub, Raleigh, both of N.C.; Jung-Chung Lin, Atlanta, Ga.

[73] Assignee: University of North Carolina at Chapel Hill, Chapel Hill, N.C.

[21] Appl. No.: 689,007

[22] Filed: Apr. 22, 1991

[51] Int. Cl.$^5$ ............... A61K 48/00; A61K 31/70; C07H 21/02
[52] U.S. Cl. .................... 514/44; 536/245; 514/934
[58] Field of Search ............... 536/27, 24.5; 435/172.3, 6; 514/44

[56] References Cited

U.S. PATENT DOCUMENTS 5,098,890 3/1992 Gewirtz et al. .............. 514/44

OTHER PUBLICATIONS

Sample et al. Proc. Natl. Acad. Sci. 83: 5096–5100, 1986.

Pagano, J. S., "From Latency to Replication: Recent Studies of the Epstein Barr Virus", presented at the Fourth International Symposium on Epstein-Barr Virus and Associated Malignant Diseases, Sep. 23–28, 1990, Huallen, Taiwan, Republic of China.

*Primary Examiner*—John W. Rollins
*Assistant Examiner*—Gary L. Kunz
*Attorney, Agent, or Firm*—Woodcock Washburn Kurtz Mackiewicz & Norris

[57] ABSTRACT

Antisense oligonucleotides and pharmaceutical compositions containing same are provided for the inhibition of Epstein-Barr virus infections. These oligonucleotides are specifically hybridizable with RNA or DNA deriving from the EBNA-1 gene of the Epstein-Barr virus. One or more oligonucleotides are used in combination to hybridize to contiguous regions of the EBNA-1 mRNA immediately downstream of the translation initiation site.

3 Claims, 2 Drawing Sheets

ANTISENSE OLIGONUCLEOTIDES AGAINST EPSTEIN-BARR VIRUS

FIELD OF THE INVENTION

This invention relates to therapies and diagnostics for latent Epstein-Barr virus (EBV) infections. In particular, this invention relates to antisense oligonucleotide interactions with certain portions of EBV RNA, which interactions have been found to lead to modulation of the effects of the viruses themselves.

BACKGROUND OF THE INVENTION

As much as 80% of the entire world population is infected with Epstein-Barr virus, a human herpesvirus. This virus is the known causative agent of self-limiting infectious mononucleosis, and is involved in the development of two well-described forms of cancer, Burkitt's lymphoma of B cell origin, and anaplastic nasopharyngeal carcinoma. EBV is also associated with polyclonal B-cell lymphomas, lymphocytic interstitial pneumonitis and hairy leukoplakia of the tongue in AIDS patients.

EBV usually enters the body via the oropharynx, where the virus replicates in epithelial cells. It is not yet clear whether the virus then becomes truly latent or if a chronic productive infection persists. It is known that in some cases the virus does not destroy the epithelial cells which it infects. Rather, the viral genome becomes fixed in the cell as an episome and the virus becomes latent, with the episome later reappearing in nasopharyngeal carcinoma. Replication in epithelial cells is thought to provide a source of virus which infects a particular class of B lymphoid cells.

EBV can be demonstrated in the B lymphocytes of nearly all EBV-seropositive individuals. The virus persists in a latent state in these lymphocytes, with expression of the viral genome thought to be limited to the EBNA-1 gene. Primary infection can be symptomatic, such as infectious mononucleosis, or silent. The virus then usually persists for the remainder of the life of the host. Reactivations, either symptomatic or silent, detectable by increases in antibody titer to viral antigens or increases in viral replication in the saliva, can occur, though the stimuli responsible are not well characterized.

While both acyclovir and azidothymidine (AZT) suppress active EBV replication, no efficacious treatment has been found for latent herpesvirus infection, including EBV. None of the inhibitors, nucleoside analogs, pyrophosphate analogs, ribonucleotide reductase inhibitors or interferons examined have shown any effect on EBV episomal number or latent infection with any of the herpesviruses.

New therapeutic strategies are greatly desired. It is particularly desired to provide compositions and methods for therapy of EBV infections which are highly effective and at the same time possess no or only minor side effects. The provision of antisense oligonucleotide therapies for latent EBV infections in accordance with this invention satisfies a long-felt need for such therapies.

OBJECTS OF THE INVENTION

It is a principal object of the invention to provide therapies for latent EBV infection.

It is a further object of the invention to provide antisense oligonucleotides which are capable of inhibiting the function of RNA of latent EBV.

Yet another object is to provide means for diagnosis of latent EBV infection.

These and other objects will become apparent from a review of the present specification.

SUMMARY OF THE INVENTION

In accordance with the present invention, oligonucleotides and oligonucleotide analogs are provided which are specifically hybridizable with DNA or RNA deriving from the EBNA-1 gene of Epstein-Barr virus. The oligonucleotide comprises nucleotide units sufficient in identity and number to effect such specific hybridization. It is preferred that the oligonucleotides or oligonucleotide analogs be specifically hybridizable with a region near the translation initiation site of the gene. It is most preferred that such oligonucleotides be used in combination so arranged as to hybridize to contiguous regions of the EBNA-1 gene immediately downstream of the translation initiation site. Such oligonucleotides and oligonucleotide analogs are conveniently and desirably presented in a pharmaceutically acceptable carrier. Other aspects of the invention are directed to methods for diagnostics and therapeutics of animals, especially humans, suspected of having a latent EBV infection. Such methods comprise contacting either the animal or cells or tissues of the animal with oligonucleotides or oligonucleotide analogs in accordance with the invention in order to inhibit the proliferation, reactivation or effect of such infection, or to effect a diagnosis thereof.

DETAILED DESCRIPTION OF THE INVENTION

Figure 1:
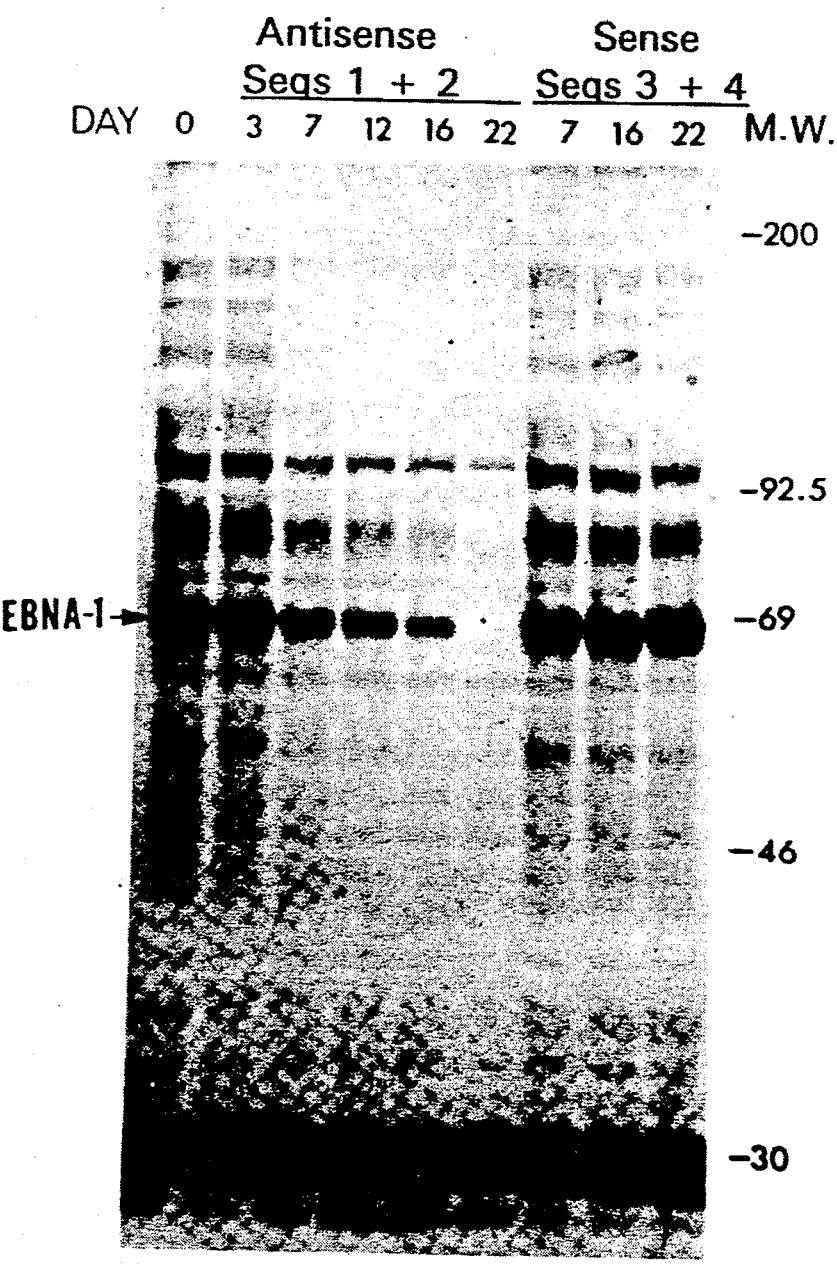
FIG. 1 is a Western blot in which relative amounts of EBNA-1 protein from EBV-infected Raji cells treated with antisense oligonucleotides or sense oligonucleotide controls are shown. Loss of the EBNA-1 protein from antisense oligonucleotide-treated cells is demonstrated.

EBV is a human herpesvirus which causes infectious mononucleosis and is implicated in the development of Burkitt's lymphoma and nasopharyngeal carcinoma. It has been well studied in part due to its unique ability to transform infected human B lymphocytes in vitro, progeny of which proliferate indefinitely, maintaining EBV in a latent state. EBV encodes about one hundred genes, of which at least eight are consistently expressed in immortalized B cell lines. These eight genes are likely to be required for the initiation and maintenance of the immortalized state of the infected cell. Of these eight, three genes, EBNA-1, EBNA-2, and BNLF-1, have been studied in detail. See Sugden, B.; Cell 57:5-7 (1989).

The EBV nuclear antigen 1 (EBNA-1) protein performs at least two functions in maintaining EBV expression in immortalized cells. It is required in trans to mediate DNA replication of the extrachromosomal viral plasmids (episomes) present in the immortalized cells. It can also trans-activate at least one viral enhancer that affects a promoter that can yield several of the transcripts present in these cells. These two functions of EBNA-1 are carried out via the binding of the EBNA-1 protein to multiple sites within the EBV plasmid origin of replication (ori-P).

Because EBNA-1 is the sole EBV gene product believed to be required for maintenance of latent EBV infection, it is an excellent target for antisense oligonucleotide inhibition. The present invention employs oligonucleotides and oligonucleotide analogs for use in antisense inhibition of the function of messenger RNAs of EBV.

In the context of this invention, the term "oligonucleotide" refers to a plurality of joined nucleotide units formed from naturally-occurring bases and furanosyl groups joined by native phosphodiester bonds. This term effectively refers to naturally occurring species or synthetic species formed from naturally occurring subunits.

"Oligonucleotide analog," as that term is used in connection with this invention, refers to moieties which function similarly to oligonucleotides but which have non-naturally occurring portions. Thus, oligonucleotide analogs may have altered sugar moieties or inter-sugar linkages. Exemplary among these are the phosphorothioate and other sulfur-containing species which are known for use in the art. They may also comprise altered base units or other modifications consistent with the spirit of this invention.

In accordance with certain preferred embodiments, at least some of the phosphodiester bonds of the oligonucleotides may be substituted with a structure which functions to enhance the ability of the compositions to penetrate into the region of cells where the RNA whose activity is to be modulated is located. It is preferred that such linkages be sulfur-containing. It is more preferred that such substitutions comprise phosphorothioate bonds. Others, such as alkyl phosphothioate bonds, N-alkyl phosphoramidates, phosphorodithioates, alkyl phosphonates, and short chain alkyl or cycloalkyl structures may also be useful. Persons of ordinary skill in the art will be able to select other linkages for use in the practice of the invention.

Oligonucleotide analogs may also include species which include at least some modified base forms. Thus, purines and pyrimidines other than those normally found in nature may be so employed. Similarly, modifications on the furanose portions of the nucleotide subunits may also occur as long as the essential tenets of this invention are adhered to.

Such analogs are best described as being functionally interchangeable with natural oligonucleotides (or synthesized oligonucleotides along natural lines), but which have one or more differences from natural structure. All such analogs are comprehended by this invention so long as they function effectively to hybridize with messenger RNA derived from the EBNA-1 gene of Epstein-Barr virus to inhibit the function of that RNA. Such oligonucleotides and analogs may, alternatively, hybridize with the corresponding DNA to similar effect.

The oligonucleotides and oligonucleotide analogs in accordance with this invention preferably comprise about 10 to about 25 subunits, preferably from about 12 to about 20 subunits, and most preferably about 18 subunits. As will be appreciated, a subunit is a base and sugar combination suitably bound to adjacent subunits through phosphodiester or other bonds.

The oligonucleotides and oligonucleotide analogs of this invention are designed to be hybridizable with messenger RNA of EBV. Such hybridization, when accomplished, interferes with the normal function of the messenger RNA. The functions of messenger RNA to be interfered may include functions such as translocation of the RNA to the site of protein translation, actual translation of protein from the RNA, and possibly even independent catalytic activity which may be engaged in by the RNA. The overall effect of such interference with the RNA function is to cause the virus to lose the benefit of the RNA and, overall, to experience interference with expression of the viral genome.

In accordance with the present invention, it is preferred to provide oligonucleotides and oligonucleotide analogs designed to interfere with messenger RNAs determined to be of significance in maintaining the latent phase of the virus, that is, the episomal form of the viral DNA, as described above. In the alternative, hybridization with the parent DNA may be achieved. In general, it has been found to be preferred to target one or more translation initiation portions of an open reading frame for antisense attack. Additional nucleotide subunits are preferably included in the oligonucleotide or oligonucleotide analog such that specific hybridization with the nucleic acid is attained to a high degree.

The oligonucleotides and oligonucleotide analogs of this invention can be used in diagnostics, therapeutics and as research reagents and kits. For therapeutic use, the oligonucleotide or oligonucleotide analog is administered to an animal, especially a human, suffering from a latent EBV infection.

The present invention is also useful in diagnostics and in research. Since the oligonucleotides and oligonucleotide analogs of this invention hybridize to EBV, sandwich and other assays can easily be constructed to exploit this fact. Provision of means for detecting hybridization of oligonucleotide or analog with latent EBV present in a sample suspected of containing it can routinely be accomplished. Such provision may include enzyme conjugation, radiolabelling or any other suitable detection systems. Kits for detecting the presence or absence of latent EBV may also be prepared.

In accordance with the teachings of the invention, two oligonucleotides were made, complementary to the region of the EBV EBNA-1 messenger RNA near the initiation codon. Two 18-base oligomers were made which hybridize to immediately contiguous regions beginning one base downstream of the EBNA-1 translation initiation site. It is believed that oligonucleotides or oligonucleotide analogs having at least a major portion of at least one of these sequences will be effective in diagnostics and therapeutics. These oligonucleotides, containing a natural phosphodiester backbone, were used together to treat Raji cells infected with EBV. In cells treated with these antisense oligonucleotides, there was a reduction in EBNA-1 protein which was progressive and generally linear over time. Cells treated with "sense" oligonucleotides (complementary to the antisense sequences) remained infected, as did untreated controls. Episomal DNA copy number was then estimated by comparison with dilutions of known copy number. In cells treated with the antisense oligomer, the episomal copy number was reduced to less than 10% of untreated control; the sense oligonucleotides had no effect. This is the first known demonstration of suppression of a latent gene product in EBV-infected cells.

The invention is further illustrated by the following example which is meant to be an illustration only and is not intended to limit the present invention to specific embodiments.

EXAMPLE $10^7$ Raji cells were pelleted at 1500 rpm and washed three times with serum-free, commercial, RPMI. Cell pellets were resuspended in 100 $\mu$l of serum-free RPMI containing 40 $\mu$M sense or antisense oligonucleotide, which had been purified on a polyacrylamide-urea gel after synthesis. In this example, "antisense oligonucleotides" refers to a mixture of equal parts of the oligonucleotide:

5' ACC TGG CCC CTC GTC AGA 3' (SEQ. I.D. NO: 1)

and the oligonucleotide:

5' GCC ATT TCC AGG TCC TGT 3' (SEQ. I.D. NO: 2), which hybridize in a contiguous manner to a region immediately downstream of the translation initiation codon (AUG) of the mRNA derived from the EBV EBNA-1 gene. Similarly, in this example, "sense oligonucleotides" consists of a mixture of equal parts of the oligonucleotide:

5' TCT GAC GAG GGG CCA GGT 3' (SEQ. I.D. NO: 3)

and the oligonucleotide:

5' ACA GGA CCT GGA AAT GGC 3' (SEQ. I.D. NO: 4), which, as will be readily apparent, are complementary to the antisense oligonucleotides listed above. Cells were incubated in the presence of oligonucleotides for one hour at 37° C. in 5% $CO_2$. Cells were then transferred to a flask containing 10 ml RPMI plus 10% fetal bovine serum. Flasks were incubated for three days at 37° C. in 5% $CO_2$. Every third day cells were counted, and aliquots taken for assay by Western and Southern blot, leaving $10^7$ cells to be treated again. The cells received a total of 8 treatments over a period of 24 days.

The Western blot prepared with human EBV-positive antiserum revealed the 67kD EBNA-1 protein in the experimental cells before treatment and in control cells throughout treatment with sense oligomers (SEQ. I.D. NOS: 3 and 4). In the cells under treatment with the antisense oligomers (SEQ. I.D. NOS: 1 and 2), there was a reduction in EBNA-1 which was progressive and linear with respect to time. The virtually complete loss of the EBNA-1 protein is shown in the Western blot in FIG. 1.

Figure 2:
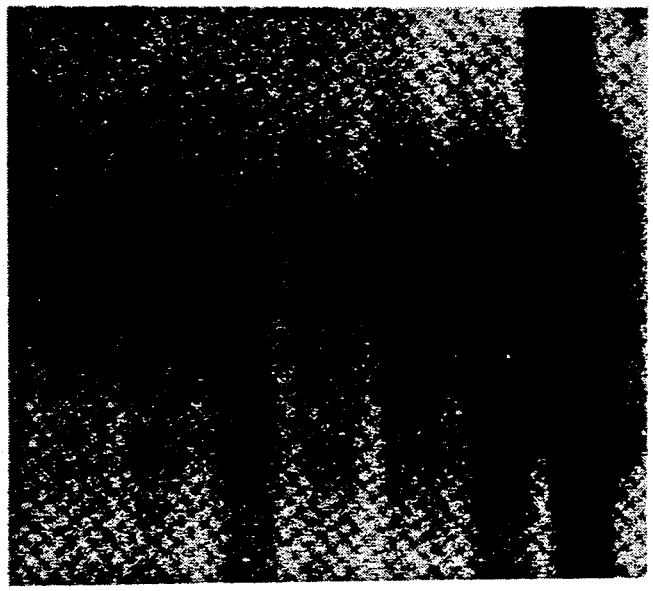
FIG. 2 is a Southern blot in which relative amounts of EBV episomal DNA from EBV-infected Raji cells treated with antisense oligonucleotides or sense oligonucleotide controls are shown. Loss of the episome from antisense oligonucleotide-treated cells is demonstrated.

This striking effect is also seen at the DNA level. Episomal copy number in Raji cells treated with antisense oligomers (SEQ. I.D. NOS: 1 and 2) was compared in Southern blot analysis to copy number in control cells treated with sense oligonucleotides (SEQ. I.D. NOS: 3 and 4). Relative amounts of episomal DNA were estimated by comparison with control reconstructions showing 50, 5, and 1 copy of the EBV genome. In cells treated with the antisense oligonucleotide, episomal copy number was reduced by at least 90%; in cells treated with the sense oligonucleotide there was no change in episomal copy number. A Southern blot demonstrating cure of oligonucleotide-treated cells is provided in FIG. 2.

---

What is claimed is:

1. An oligonucleotide or oligonucleotide analog consisting essentially of 12 to 20 nucleotides, possessing at least one substituted phosphodiester internucleotide linkage, having a sequence within Sequence ID No. 1, and hybridizable with the EBNA-1 gene mRNA.

2. An oligonucleotide or oligonucleotide analog consisting essentially of 12 to 20 nucleotides, possessing at least one substituted phosphodiester internucleotide linkage, having a sequence within Sequence ID No. 2., and hybridizable with EBNA-1 gene mRNA.

3. A pharmaceutical composition comprising:

a) an oligonucleotide or oligonucleotide analog consisting essentially of 12 to 20 nucleotides possessing at least one substituted phosphodiester internucleotide linkage, having a sequence within Sequence ID No. 1, and hybridizable with the EBNA-1 gene mRNA;

b) an oligonucleotide or oligonucleotide analog consisting essentially of 12 to 20 nucleotides, possessing at least one substituted phosphodiester internucleotide linkage, having a sequence within Sequence ID No. 2., and hybridizable with EBNA-1 gene mRNA; and c) a pharmaceutically acceptable carrier.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: unknown ( x i ) SEQUENCE DESCRIPTION: SEQ ID NO: 1:

ACCTGGCCCC TCGTCAGA          18

( 2 ) INFORMATION FOR SEQ ID NO: 2:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: unknown ( x i ) SEQUENCE DESCRIPTION: SEQ ID NO: 2:

GCCATTTCCA GGTCCTGT          18

( 2 ) INFORMATION FOR SEQ ID NO: 3:

( i ) SEQUENCE CHARACTERISTICS:
        ( A ) LENGTH: 18
        ( B ) TYPE: nucleic acid (C) STRANDEDNESS: single
(D) TOPOLOGY: unknown (xi) SEQUENCE DESCRIPTION: SEQ ID NO: 3:

TCTGACGAGG GGCCAGGT 18

(2) INFORMATION FOR SEQ ID NO: 4:

(i) SEQUENCE CHARACTERISTICS:
(A) LENGTH: 18
(B) TYPE: nucleic acid
(C) STRANDEDNESS: single
(D) TOPOLOGY: unknown (xi) SEQUENCE DESCRIPTION: SEQ ID NO: 4:

ACAGGACCTG GAAATGGC 18